United States Patent
Suter et al.

(10) Patent No.: US 8,523,566 B2
(45) Date of Patent: Sep. 3, 2013

(54) DRILL SLEEVE FOR A DENTAL DRILL

(75) Inventors: Edmund Suter, Niederdorf (CH); Steffen Kühne, Möhlin (CH); Patrick Streff, Weil am Rhein (DE)

(73) Assignee: Straumann Holding AG, Basel (CH)

( * ) Notice: Subject to any disclaimer, the term of this patent is extended or adjusted under 35 U.S.C. 154(b) by 42 days.

(21) Appl. No.: 12/627,221

(22) Filed: Nov. 30, 2009

(65) Prior Publication Data
US 2010/0136500 A1    Jun. 3, 2010

(30) Foreign Application Priority Data
Dec. 1, 2008 (EP) .................................... 08020834

(51) Int. Cl.
*A61C 8/00* (2006.01)
(52) U.S. Cl.
USPC ............................................................ 433/72
(58) Field of Classification Search
USPC .................................... 433/72, 74, 75, 76
See application file for complete search history.

(56) References Cited

U.S. PATENT DOCUMENTS

| | | | |
|---|---|---|---|
| 5,015,183 A | 5/1991 | Fenwick | |
| 5,133,660 A | 7/1992 | Fenick | |
| 5,556,278 A * | 9/1996 | Meitner | 433/75 |
| 5,888,034 A | 3/1999 | Greenberg | |
| 5,915,962 A | 6/1999 | Rosenlicht | |
| 5,954,769 A | 9/1999 | Rosenlicht | |
| 5,967,777 A * | 10/1999 | Klein et al. | 433/75 |
| 5,989,025 A * | 11/1999 | Conley | 433/76 |
| 7,942,668 B2 * | 5/2011 | Brajnovic et al. | 433/76 |
| 2003/0157457 A1 | 8/2003 | Blacklock | |
| 2004/0142300 A1 | 7/2004 | Aravena | |
| 2004/0219477 A1 | 11/2004 | Harter | |
| 2004/0219479 A1 | 11/2004 | Malin et al. | |
| 2004/0219481 A1 | 11/2004 | Malin et al. | |
| 2005/0170311 A1 | 8/2005 | Tardieu | |
| 2006/0240378 A1 | 10/2006 | Weinstein et al. | |
| 2006/0263743 A1 | 11/2006 | Tedesco | |
| 2007/0077532 A1 | 4/2007 | Harter | |
| 2008/0064005 A1 | 3/2008 | Meitner | |
| 2008/0166681 A1 | 7/2008 | Weinstein et al. | |
| 2008/0220390 A1 * | 9/2008 | Klein | 433/76 |
| 2009/0011382 A1 * | 1/2009 | Bavar | 433/76 |

FOREIGN PATENT DOCUMENTS

| | | |
|---|---|---|
| DE | 299 09 616 U1 | 6/1999 |
| DE | 20 2006 004 954 U1 | 3/2006 |
| DE | 102005023028 | 11/2006 |
| EP | 1 894 539 A1 | 9/2006 |

(Continued)

OTHER PUBLICATIONS

May 14, 2009 EP Search Report in corresponding EP No. 08020834.1-2318.

*Primary Examiner* — Ralph Lewis
(74) *Attorney, Agent, or Firm* — Novak Druce Connolly Bove & Quigg LLP

(57) ABSTRACT

Drill sleeve (1) for a dental drill (70) having a hollow and cylindrical shape and a longitudinal axis A, a circular inner surface (10) for guiding the dental drill (70), and an outer surface (15) intended to be inserted into a template (50). The outer surface (15) of the drill sleeve (1) has at least one longitudinal flattened or concave area (20, 120), the circular inner surface (10) is essentially parallel to the longitudinal axis A, and the drill sleeve (1) is thin-walled.

31 Claims, 3 Drawing Sheets

(56) References Cited

FOREIGN PATENT DOCUMENTS

| | | |
|---|---|---|
| EP | 2 060 240 A2 | 11/2008 |
| WO | WO 94/00073 A1 | 1/1994 |
| WO | WO97/43981 A1 | 11/1997 |
| WO | WO97/49351 A1 | 12/1997 |
| WO | WO 03/071972 A1 | 9/2003 |
| WO | WO2005/053566 A | 6/2005 |
| WO | WO 2006/014130 A1 | 2/2006 |
| WO | WO2006/130067 A1 | 12/2006 |
| WO | WO 2007/067105 A1 | 6/2007 |
| WO | WO 2007/077223 A1 | 7/2007 |
| WO | WO 2007/079775 A1 | 7/2007 |
| WO | WO2007/104842 A1 | 9/2007 |
| WO | WO 2008/089885 A1 | 7/2008 |

* cited by examiner

DRILL SLEEVE FOR A DENTAL DRILL

FIELD OF THE INVENTION

The present invention relates to a drill sleeve for a dental drill, to a set or template comprising the drill sleeve, and to its use for guiding a dental drill.

BACKGROUND

In dental treatment, it is well known to replace a missing tooth by an endosseous dental implant with an artificial crown. Typically, screw-shaped dental implants are used, such as the ones described by Brånemark in WO 97/49351. In order to anchor the implant in a patient's jaw-bone, a suitable drill hole is applied to the bone and the dental implant is fixed therein.

When the drill hole is applied to the jaw-bone, it is very important that the position, depth, width, and orientation of the drill hole are accurately adjusted to the patient's dental and osseous anatomy. A faulty drilling trajectory is very difficult to correct and can cause damage to nearby structures, such as the inferior alveolar nerve; it can also cause pain to the patient and, in some cases, even implant failure. In order to avoid deviations from the optimal drilling position and orientation, it is known to use a custom-made surgical template having an exact mating region in the mouth of the patient (either on the jaw-bone, the gums or the remaining teeth), which has bore tubes with the predetermined positions and orientations. Into these bore tubes, drill sleeves are inserted, which serve to guide the drills used for creating the implant drill holes in the jaw of the patient. Such a template with drill sleeves is described in U.S. Pat. No. 5,015,183, WO 2006/041430, and WO 97/43981, for example.

The drill sleeves are typically of hollow cylindrical shape and made of metal. During the drilling process, the drill sleeve's circular inner surface serves as guidance for the drill. To this end, it is known to place a secondary guiding element inside the drill sleeve, such as a drill spoon or a guiding cylinder, which can be exchanged in the course of the drilling process. The use of a drill sleeve in combination with a secondary guiding element is described in WO 2006/130067 or DE 10 2005 023 028, for instance. This approach is particularly favorable if several drills of increasing diameters are used for preparing the drill hole. Accordingly, several secondary guiding elements may be placed, one after the other, inside the same drill sleeve, each corresponding to a certain drill diameter. Alternatively, it is also possible that the drill is guided directly by the drill sleeve itself.

For applying the drill hole to the patient's jaw-bone, the dental drill is inserted into the drill sleeve, optionally containing a secondary guiding element, and then the hole is drilled in the axial direction of the drill sleeve. If the space above the implantation area is limited, especially in the case where a back tooth has to be replaced, it may be difficult to insert the drill axially into the drill sleeve. In order to overcome this problem, drill sleeves having a longitudinal slit have been described in WO 2007/104842. With these slitted drill sleeves, it is possible to insert the drill sideways, which considerably facilitates the insertion of the drill into the drill sleeve.

If, however, the space in the implantation area is limited in the lateral direction, especially if several adjacent implants are to be placed within the same tooth gap, there may not be enough space to place all drills sleeves necessary within the gap. In addition, if two adjacent drill sleeves placed into the template are at close quarters, the remaining template between the bore tubes for the drill sleeves may break. Accurate drilling of the drill hole can thus no longer be guaranteed.

It would therefore by desirable to provide a means for guiding a dental drill, which is suitable for use in implantation areas with laterally limited space.

SUMMARY OF THE INVENTION

A drill sleeve according to one embodiment of the present invention has an essentially hollow cylindrical shape and a longitudinal axis, a circular inner surface for guiding a dental drill, and an outer surface intended to be inserted into a template. The outer surface of the drill sleeve has at least one longitudinal flattened area, whereas the inner surface of the drill sleeve has a circular cross section. In addition, the circular inner surface of the drill sleeve is essentially parallel to the longitudinal axis, and the drill sleeve is thin-walled. Thus, the drill sleeve has, in the at least one longitudinal flattened area, a smaller wall thickness than in the other areas of the drill sleeve. The at least one longitudinal flattened area is oriented in the axial direction of the drill sleeve and has a planar outer surface. The circular inner surface, which is intended to serve as a guide area for a dental drill, extends parallel to the longitudinal axis of the drill sleeve and thus also parallel to circular part of the outer surface of the drill sleeve. In a preferred embodiment, the drill sleeve's coronal and apical end surfaces are at least essentially perpendicular to the drill sleeve's longitudinal axis and thus also to its longitudinal flattened area and its circular inner surface.

The wall thickness of the drill sleeve in one embodiment is as thin as possible. As space is typically rather limited in a patient's oral cavity, it is advantageous if the drill sleeve takes up as little space as possible. On the other hand, the drill sleeve needs to have a certain minimal wall thickness in order to guarantee safe and reliable operation. The thin-walled drill sleeve preferably has, for instance, a wall thickness of about 0.2 to 1.5 mm, and more preferably of 0.4 to 1.3 mm.

According to another embodiment of the invention, the essentially hollow cylindrical drill sleeve has at least one longitudinal concave area, where the wall thickness is also smaller than in the other areas of the drill sleeve. The at least one longitudinal concave area is oriented in the axial direction of the drill sleeve. Again, the thin-walled drill sleeve has a longitudinal axis and a circular inner surface for guiding the dental drill, which is essentially parallel to the longitudinal axis of the drill sleeve.

The drill sleeve according to various embodiments is suitable for being inserted into a bore tube in a surgical template adjusted to a patient's mouth, thus defining a drilling trajectory. The circular inner surface of the drill sleeve is suitable for holding a secondary guiding element and/or for guiding a dental drill directly. Due to the at least one longitudinal flattened area in the outer surface, the drill sleeve requires less space and may be used in small tooth gaps with limited space.

In one embodiment, the outer surface of the drill sleeve has exactly one longitudinal flattened area. Such a drill sleeve is especially well suited for gaps, into which two dental implants are to be placed. If each of the drill sleeves is oriented such that the two longitudinal flattened areas are facing each other, the distance between the two drill sleeves can be minimized without risking breakage of the intervening template.

In another embodiment, the outer surface of the drill sleeve has two longitudinal flattened areas. A drill sleeve having two flattened areas allows for a further minimization of the space required between one drill sleeve and a vicinal second drill sleeves or tooth. When inserting the drill sleeve into the template, it is particularly preferred to arrange the sleeve such that the two flattened areas are oriented in the direction of the vicinal second drill sleeves or teeth. Depending on the implantation position and the orientation of the surrounding teeth or implants, it may be most preferred that the two longitudinal flattened areas of the outer surface are diametrically opposed or that the two flattened areas are arranged in a certain angle.

In another embodiment, the at least one longitudinal flattened or concave area is parallel to the longitudinal axis of the drill sleeve. Such an orientation facilitates the insertion of the drill sleeve into a bore in a drill template.

In another embodiment, the at least one longitudinal flattened or concave area extends over the full length of the drill sleeve, i.e. from its coronal end to its apical end surfaces. Again, this facilitates the insertion of the drill sleeve into a bore in a drill template.

In another embodiment, the outer surface of the drill sleeve has a gripping surface. Such a gripping surface not only allows for safe handling of the drill sleeve before it is inserted into the template, but also improves the anchorage of the drill sleeve in the template. In one preferred embodiment, the outer surface of the drill sleeve has several longitudinal projections in addition to the flattened area. These projections inhibit rotation of the drill sleeve during the drilling process, thus improving the accuracy of the drilling and minimizing the stress exerted on the template. In a preferred embodiment, the longitudinal projections are interrupted by at least one essentially circular groove. By interaction of such a groove with a corresponding protrusion in the surrounding template, a vertical displacement of the drill sleeve within the template is inhibited. Alternatively, the outer surface of the drill sleeve is roughened in order to serve as a gripping surface.

In another embodiment, the outer surface of the drill sleeve has a gripping surface in the form of longitudinal recesses and protrusions and at least one, preferably two, essentially circular grooves (see for instance FIG. 2). Such a drill sleeve may have, according to one preferred embodiment, an inner diameter of 5.7 mm, a minimal outer diameter of 5.9 mm, and a maximal outer diameter of 6.3 mm. According to another preferred embodiment, the drill sleeve has an inner diameter of 2.8 mm, a minimal outer diameter of 3.2 mm, and a maximal outer diameter of 3.8 mm. The height of these drill sleeves is preferably about 3 to 8 mm, more preferably about 5 to 6 mm, for instance 5 or 6 mm.

In another embodiment, the drill sleeve has a longitudinal slit. Such a slitted drill sleeve allows for inserting the drill sideways, which is particularly favorable if the space above the implantation area is limited and an axial insertion is difficult or even impossible. The longitudinal slit is preferably narrower than one third of the drill sleeve's circumference, in order to guarantee precise guiding of the drill. At the same time, the longitudinal slit is preferably wider than the diameter of the dental drill.

For drill sleeves having a longitudinal slit, it is particularly preferable that the rotation of the drill sleeve during the drilling process is inhibited. Therefore, it is preferred that a drill sleeve comprising a longitudinal slit also has a gripping surface, and, in particular, that the drill sleeve's outer surface has several longitudinal projections.

In another embodiment, the drill sleeve has a circumferential flange at its coronal end. Due to such a circumferential flange, the fixation of the drill sleeve in the template is improved and, in particular, the drill sleeve cannot be pushed further into the template during the drilling process. Therefore, greater stability of the template-drill sleeve assembly is achieved and the accuracy of the drilling can be maximized.

Preferably, the drill sleeve is made of stainless steel. A drill sleeve of stainless steel is relatively inexpensive and guarantees precise guiding of the dental drill. In addition, it allows for facile sterilization in case the drill sleeve is used more than once.

The present invention also relates to a set comprising one or more drill sleeves according to the prior embodiments. Said set preferably includes several drill sleeves, the drill sleeves' circular inner surfaces having differing diameters and/or differing lengths. Such a set provides a choice of drill sleeves which may be chosen by the dental surgeon according to the patient's anatomy.

The present invention also relates to a template comprising one or more drill sleeves according to the prior embodiments.

The present invention also relates to the use of a drill sleeve according to the prior embodiments for guiding a dental drill. The drill sleeve is preferably used in combination with a secondary guiding element inserted into the drill sleeve. Alternatively, the drill may be guided directly by the inner surface of the drill sleeve. The use of a drill sleeve according to the prior embodiments is particularly favorable if, in the lateral direction, the space around the implantation position is limited.

BRIEF DESCRIPTION OF THE DRAWINGS

Embodiments of the invention will be described, by way of example only, with reference to the accompanying drawings, in which.

DETAILED DESCRIPTION

Figure 1:
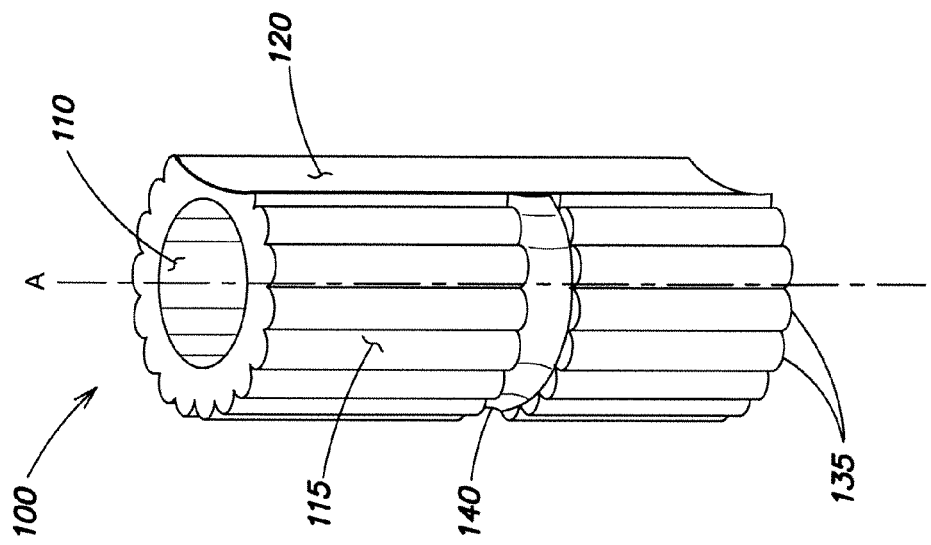
FIG. 1 is a schematic perspective view of a first embodiment of a drill sleeve of the present invention.

The embodiment of the drill sleeve 1 shown in FIG. 1 is of essentially hollow cylindrical shape and is entirely made of stainless steel. It has a longitudinal axis A, a circular inner surface 10 for guiding a drill, and an outer surface 15, which is intended to be inserted into a template. The outer surface 15 as shown in FIG. 1 comprises one longitudinal flattened area 20. However, the outer surface 15 may have more than one longitudinal flattened area 20. At its coronal end 25, the drill sleeve 1 has a circumferential flange 30.

Figure 2:
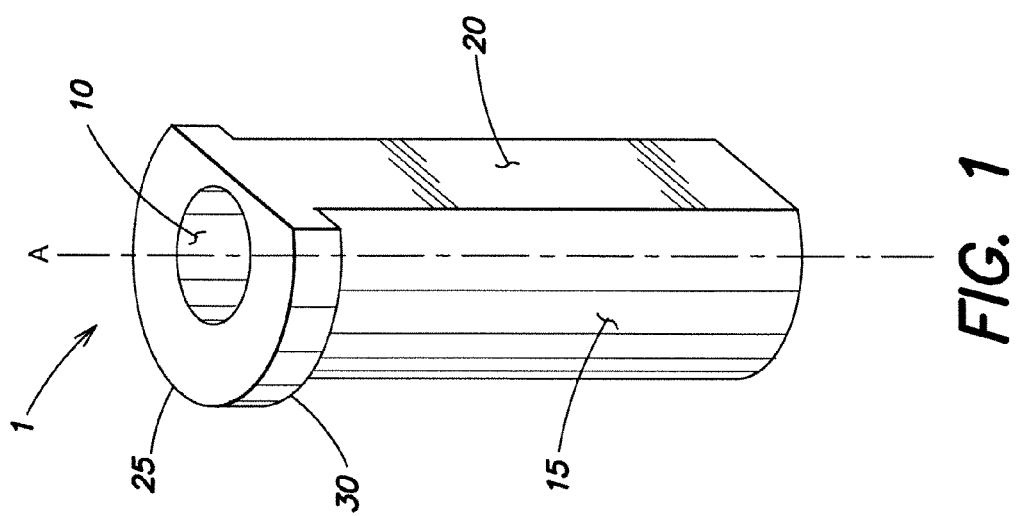
FIG. 2 is a schematic perspective view of a second embodiment of a drill sleeve of the present invention.

A second embodiment of the drill sleeve 100 shown in FIG. 2 also has a longitudinal axis A, a circular inner surface 110, and an outer surface 115 with a longitudinal concave area 120. In addition to the concave area 120, the outer surface 115 also has several longitudinal projections 135, which are interrupted by an essentially circular groove 140.

Figure 3:
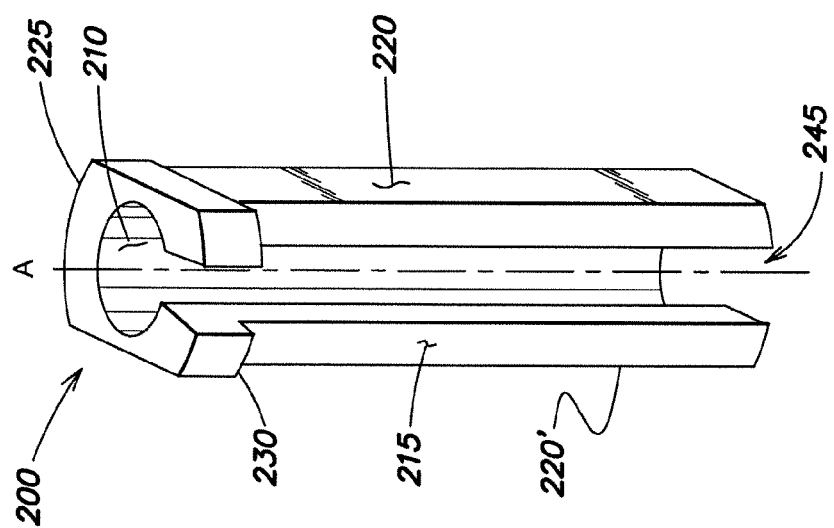
FIG. 3 is a schematic perspective view of a third embodiment of a drill sleeve of the present invention.

In a third embodiment shown in FIG. 3, the outer surface 215 of the drill sleeve 200 comprises two longitudinal flattened areas 220, 220', and, at its coronal end 225, a circumferential flange 230. This embodiment of the drill sleeve 200 is further characterized by a longitudinal slit 245.

Figure 4:
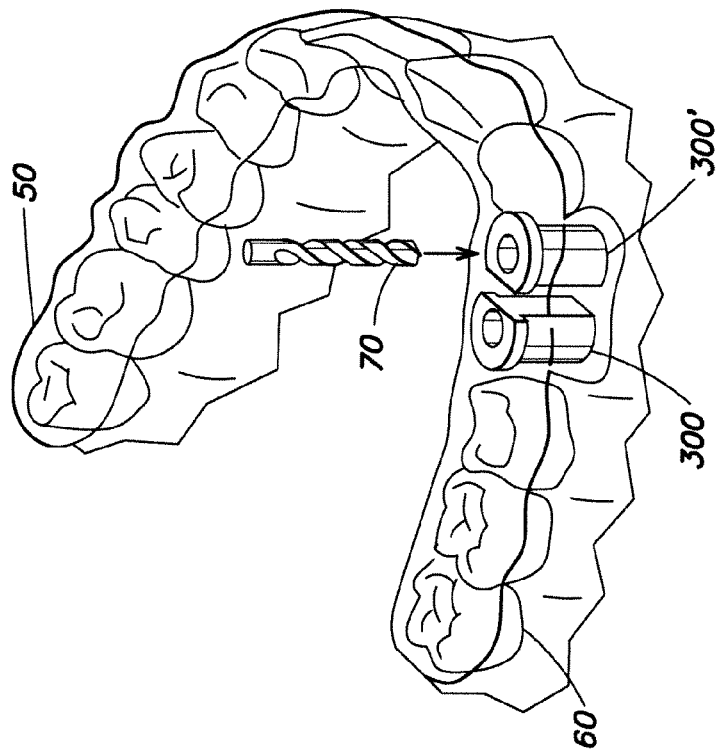
FIG. 4 is a schematic perspective view of a template including two drill sleeves according to another embodiment of the present invention.
Figure 5:
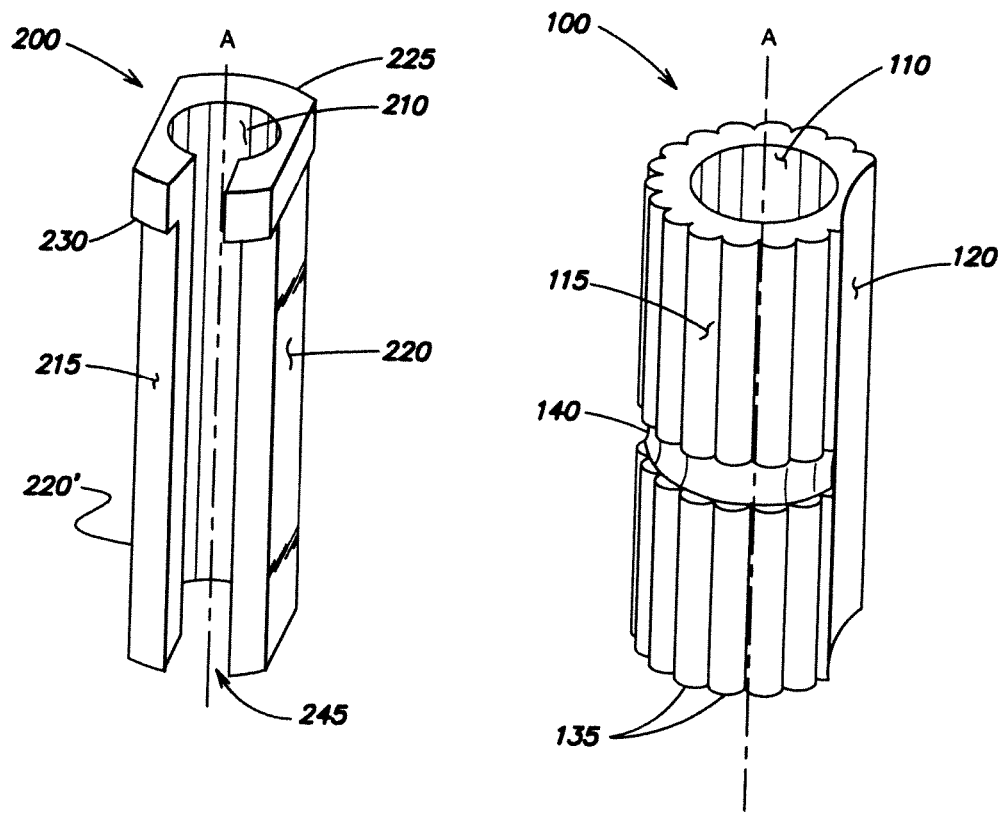
FIG. 5 is a schematic perspective view of several drill sleeves according to another embodiment of the present invention.

FIG. 4 is a schematic representation of a template 50, which is placed on a patient's dentition 60. The template 50 includes two drill sleeves 300, 300' according to any of prior embodiments of the present invention, which are inserted into the template 50 at the implantation position. In order to prepare a drill hole in the patient's jaw-bone, the dental surgeon will insert a drill 70 through the drill sleeves 300, 300', using the drill sleeves 300, 300' as guidance for the drill 70. FIG. 5 is a schematic representation showing a set of several drill sleeves 100 and 200 of differing diameters and lengths as previously shown and described with respect to FIGS. 2-3.

The invention claimed is:

1. A drill sleeve for a dental drill, comprising:
   an essentially hollow cylindrical shape and a longitudinal axis,
   a circular inner surface for guiding the dental drill and an outer surface intended to be inserted into a template,
   wherein the outer surface has at least one longitudinal flattened or concave area that extends over the full length of the drill sleeve and wherein the outer surface has longitudinal projections extending essentially over the full length of the drill sleeve,
   wherein the circular inner surface is essentially parallel to the longitudinal axis, and the drill sleeve has a wall thickness ranging from 0.2 mm to 1.5 mm,
   and wherein the outer surface has two longitudinal flattened areas, which are diametrically opposed.

2. Drill sleeve according to claim 1, wherein the at least one longitudinal flattened area is parallel to the longitudinal axis of the drill sleeve.

3. Drill sleeve according to one of claim 1, wherein the outer surface has a gripping surface comprising at least one circular groove.

4. Drill sleeve according to claim 1, wherein the longitudinal projections are interrupted by at least one essentially circular groove.

5. Drill sleeve according to claim 1, wherein the sleeve has a longitudinal slit.

6. Drill sleeve according to claim 5, wherein the longitudinal slit is narrower than one third of the drill sleeve's circumference.

7. Drill sleeve according to claim 5, wherein the longitudinal slit is wider than the diameter of the dental drill.

8. Drill sleeve according to one of claim 1, wherein the sleeve has a circumferential flange at its coronal end.

9. Drill sleeve according to claim 1, wherein the sleeve is made of stainless steel.

10. A set comprising several drill sleeves according to claim 1.

11. Set according to claim 10, comprising several drill sleeves having circular inner surfaces with at least one of differing diameters and differing lengths.

12. Template comprising one or more drill sleeves according to claim 1.

13. Method comprising use of a drill sleeve according to claim 1 in guiding a dental drill.

14. Method according to claim 13, including providing the drill sleeve in a surgical template and using the drill sleeve as a drilling trajectory for the dental drill.

15. Method according to claim 14, including providing two adjacent drill sleeves in the template oriented with their longitudinal flattened or concave areas vicinal to one another.

16. A drill sleeve for a dental drill, comprising:
   an essentially hollow cylindrical shape and a longitudinal axis,
   a circular inner surface for guiding the dental drill and an outer surface intended to be inserted into a template,
   wherein the outer surface has at least one longitudinal flattened or concave area that extends over the full length of the drill sleeve,
   wherein the circular inner surface is essentially parallel to the longitudinal axis,
   and the drill sleeve has a wall thickness ranging from 0.2 mm to 1.5 mm,
   and wherein the outer surface has longitudinal projections, which are interrupted by at least one essentially circular groove.

17. Drill sleeve according to claim 16, wherein the longitudinal area is flattened.

18. Drill sleeve according to claim 16, wherein the outer surface has exactly one longitudinal flattened area.

19. Drill sleeve according to claim 16, wherein the outer surface has two longitudinal flattened areas.

20. Drill sleeve according to claim 19, wherein the two longitudinal flattened areas of the outer surface are diametrically opposed.

21. Drill sleeve according to claim 16, wherein the at least one longitudinal flattened or concave area is parallel to the longitudinal axis of the drill sleeve.

22. Drill sleeve according to claim 16, wherein the sleeve has a longitudinal slit.

23. Drill sleeve according to claim 22, wherein the longitudinal slit is narrower than one third of the drill sleeve's circumference.

24. Drill sleeve according to claim 22, wherein the longitudinal slit is wider than the diameter of the dental drill.

25. Drill sleeve according to claim 16, wherein the sleeve has a circumferential flange at its coronal end.

26. Drill sleeve according to claim 16, wherein the sleeve is made of stainless steel.

27. Set comprising several drill sleeves according to claim 16.

28. Set according to claim 27, comprising several drill sleeves having circular inner surfaces with at least one of differing diameters and differing lengths.

29. Template comprising one or more drill sleeves according to claim 16.

30. Method comprising use of a drill sleeve according to claim 16 in guiding a dental drill.

31. Method according to claim 30, including providing the drill sleeve in a surgical template and using the drill sleeve as a drilling trajectory for the dental drill.

* * * * *